United States Patent [19]
Rivard

[11] Patent Number: 5,413,576
[45] Date of Patent: May 9, 1995

[54] APPARATUS FOR TREATING SPINAL DISORDER

[76] Inventor: Charles-Hilaire Rivard, 308 Curzon Avenue, St. Lambert, Quebec, Canada, J4P 2V5

[21] Appl. No.: 15,919
[22] Filed: Feb. 10, 1993
[51] Int. Cl.⁶ .............................................. A61B 17/56
[52] U.S. Cl. ........................................................ 606/61
[58] Field of Search .................... 606/61, 60, 62, 69

[56] References Cited

U.S. PATENT DOCUMENTS

| | | | |
|---|---|---|---|
| 4,041,939 | 8/1977 | Hall | 606/61 |
| 5,084,049 | 1/1992 | Asher et al. | 606/60 |
| 5,133,716 | 7/1992 | Plaza | 606/61 |

FOREIGN PATENT DOCUMENTS

| | | | |
|---|---|---|---|
| 1262322 | 10/1989 | Canada . | |
| 1292653 | 12/1991 | Canada . | |
| 1298750 | 4/1992 | Canada . | |
| 2244446 | 4/1975 | France . | |
| 2645427 | 10/1990 | France | 606/61 |
| 3032237 | 3/1982 | Germany . | |
| 1034123 | 6/1966 | United Kingdom . | |
| 2096465 | 10/1982 | United Kingdom . | |
| 1544409 | 2/1990 | U.S.S.R. | 606/61 |

*Primary Examiner*—Tamara L. Graysay
*Attorney, Agent, or Firm*—Foley & Lardner

[57] ABSTRACT

An internal brace system includes a pair of implantable rods for mounting on either side of the spinal column co-extensive with a portion of the spinal column to be treated. Transverse bars rigidly connect the rods together in spaced-apart parallel arrangement to provide a unitary internal brace stabilizing structure. Pairs of anchors in the form of cuffs are provided with one of each pair on respective transverse processes of each selected vertebra in the portion of the spinal column to be treated. A flexible first tie member extends from each anchor cuff to a sleeve on a respective rod on either side of the spinal column for retaining individual vertebra in a predetermined location relative to the internal brace system and against torsional forces applied through the spinal column. A further anchor is provided on the spinous process of the selected vertebra. Second flexible tie members extend from the respective cuffs on the transverse processes to the anchor on the spinous process in order to prevent the cuffs from slipping off the transverse processes.

11 Claims, 3 Drawing Sheets

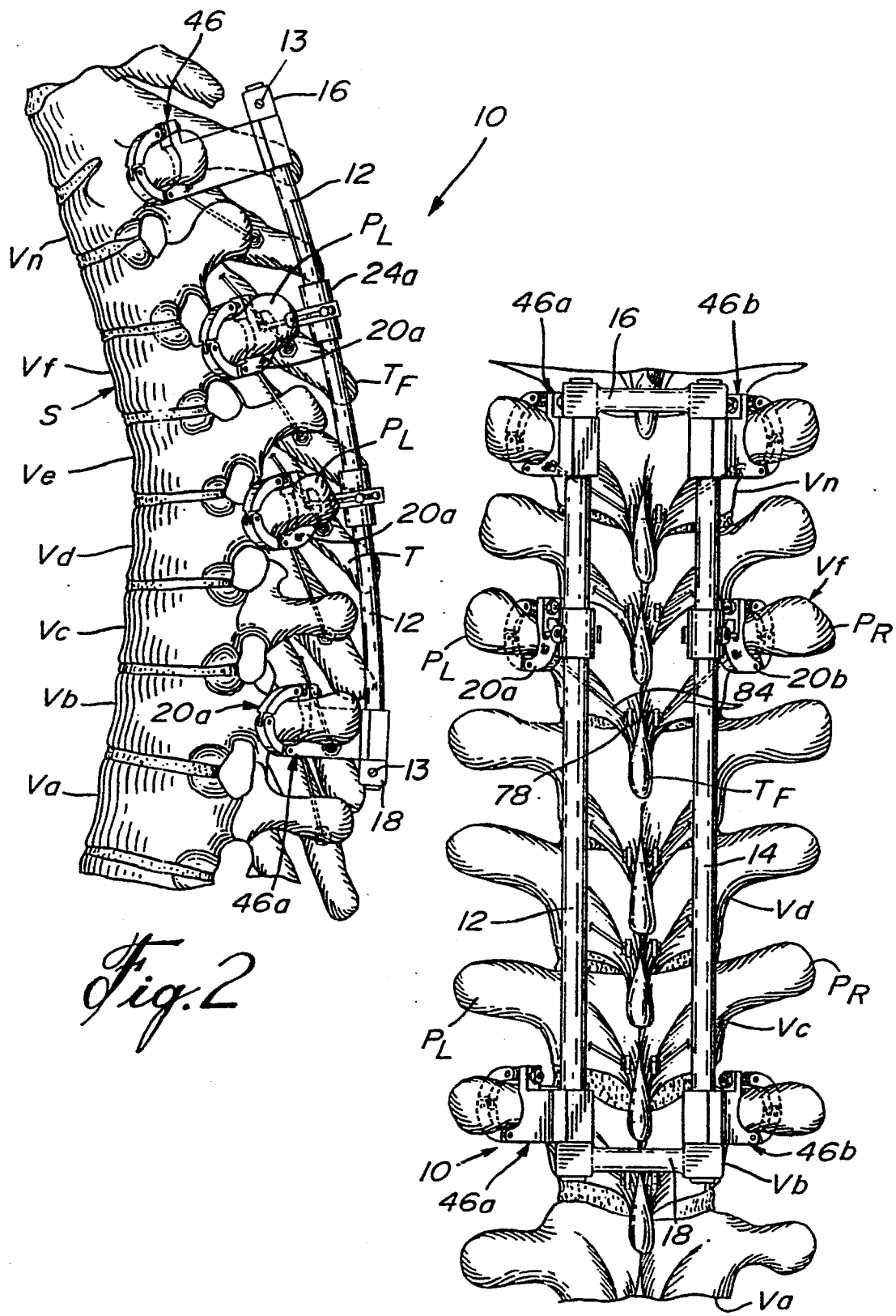

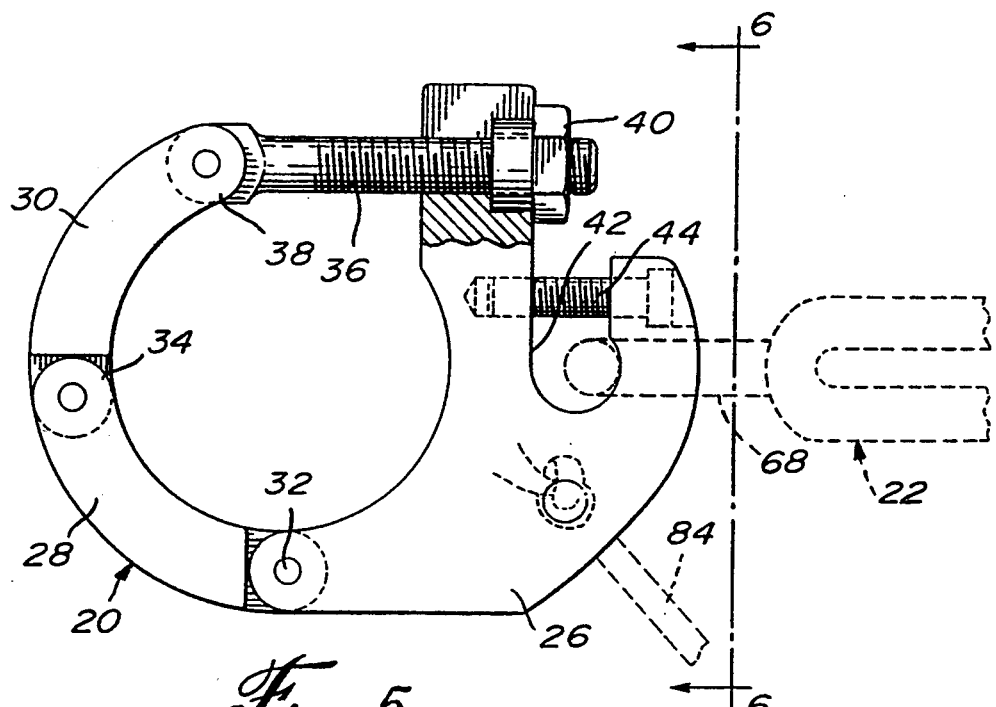
Fig. 5
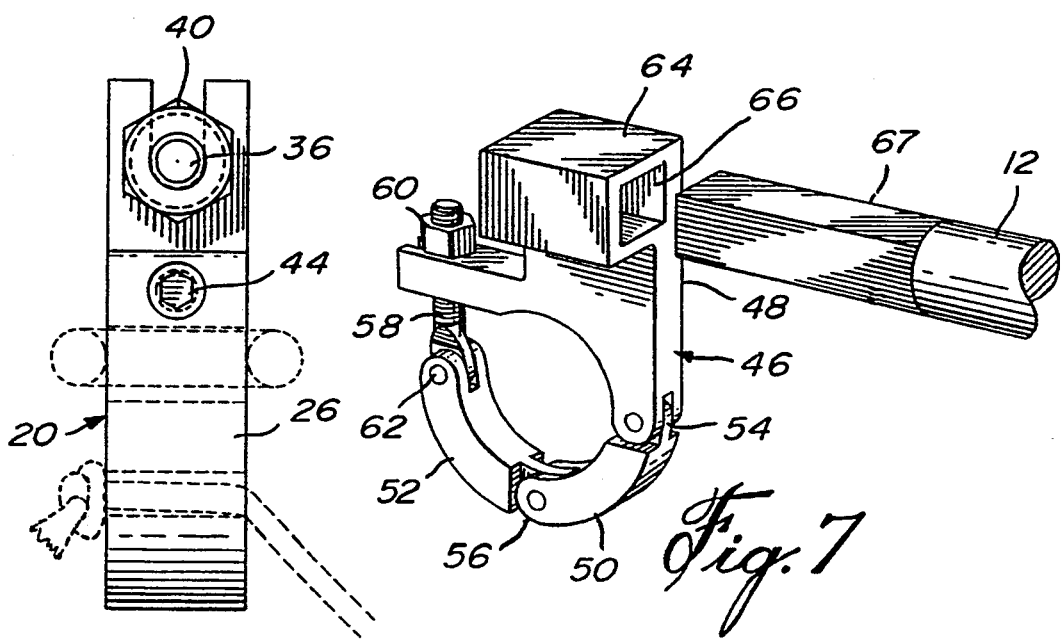
Fig. 6
Fig. 7

5,413,576

APPARATUS FOR TREATING SPINAL DISORDER

BACKGROUND OF THE INVENTION

1. Field of the Invention

The present invention relates to an apparatus for use in the treatment of scoliosis.

2. Description of the Prior Art

Prior to 1962, scoliosis was treated with various external casts and/or bone grafts. Successive body casts of ever increasing height would be utilized to try to correct the spine from a disorder such as a lateral curve in the spinal column. External braces would still be employed in the treatment of minor scoliosis. However in the event of severe deformity of the spine, major surgery involving bone grafts and the fusion of several vertebrae would be the only solution. The bone grafts and vertebrae fusion would sometimes cause serious complications throughout the patient's adult life.

In 1962, Paul Harrington proposed the use of implantable stainless steel rods which were placed adjacent the vertebral bodies and hooks on the rods were inserted under the laminae of selected vertebra. An excellent summary of the prior art devices based on the Harrington procedures can be found in U.K. patent application G.B. 2 096 465 A published Oct. 20, 1982 in the name of Kevin A. Bobechko. However it has since been found that it is still necessary to supplement the stainless steel rod with bone grafts as described in the Bobechko patent application.

Canadian Patent 1,262,322 issued Oct. 17, 1989 to Yves Cotrel also described a rod and hook system. Cotrel mounts the hooks with hook brackets to the vertebrae and then the hook brackets can be connected to a pair of rods as shown in FIG. 12. The assembly is rigid in that the hook brackets are locked to the rods against rotational or longitudinal movement. That section of the spine is thus kept rigid. However given the lack of flexibility, and the fact that the loads are completely transferred to the rod assembly, the assembly is not considered sufficiently strong and thus bone graft and fusion of the vertebrae must also be resorted to.

SUMMARY OF THE INVENTION

It is an aim of the present invention to provide an internal brace system to correct the spine disorder in the treatment of scoliosis.

It is a further aim of the present invention to provide an internal system which will eliminate the need in most cases of resorting to bone graft to supplement the support offered by the system.

It is still a further aim of the present invention to provide an internal brace system which will rely on normal loads being transmitted through the spine including the portion of the spine being subjected to treatment.

It is a further aim of the present invention to provide an internal brace system which would avoid the introduction of extraneous elements within the spinal canal such as hooks or wires.

It is a further aim of the present invention to provide an internal brace system made of material which is sufficiently strong to resist normal forces and loads which will be subjected to the spinal column and internal brace system.

A construction in accordance with the present invention comprises an internal brace system including at least a pair of implantable rods for mounting on either side of the spinal column coextensive with a portion of the spinal column to be treated, means for rigidly connecting the rods together in spaced apart parallel arrangement to provide a unitary internal brace stabilizing structure, pairs of anchor means provided one of each pair on respective transverse processes of each selected vertebra in the portion of the spinal column to be treated, first tie means extending from each anchor means to connection means on a respective rod on either side of the spinal column for retaining individual vertebra in a predetermined location relative to the internal brace system and against torsional forces applied through the spinal column.

In a more specific embodiment of the present invention, a further anchor means is provided on the spinous process of the selected vertebra, the anchors on the transverse processes are in the form of cuffs mounted on each transverse process and second tie means extend from the respective cuffs on the transverse processes to the anchor on the spinous process in order to prevent the cuffs from slipping off the transverse processes.

In a still more specific embodiment of the present invention, the means for connecting the first tie means to the respective rods includes a plurality of separate sleeves on the rods adapted to slide thereon and each first tie means is connected to a respective sleeve.

Thus, an internal brace system is provided to retain individual vertebra in a position approximating a correct position in a normal spine. The provision of at least a pair of rods in a unitary structure with tie means from each rod to a corresponding transverse process of a vertebra, retains the vertebra against the torsional forces inherent in the disorder which would cause the vertebra to rotate in the horizontal plane of the vertebra. The fact that the tie means are flexible permits loads to be transmitted through the portion of the spine coextensive with the internal brace system. The portion of the spinal column also has a limited flexibility since bone grafts are not used.

BRIEF DESCRIPTION OF THE DRAWINGS

Having thus generally described the nature of the invention, reference will now be made to the accompanying drawings, showing by way of illustration, a preferred embodiment thereof, and in which:

FIG. 1 is a rear elevation view of an embodiment of the internal brace system in accordance with the present invention as it would appear on a portion of a spinal column;

FIG. 2 is a side elevation of the embodiment shown in FIG. 1;

FIG. 5 is a plan view partly in crosssection of a detail shown in FIG. 3;

FIG. 6 is an end elevation of the detail shown in FIG. 5; and

FIG. 7 is a fragmentary perspective view showing a modified version of the detail shown in FIGS. 5 and 6.

DESCRIPTION OF THE PREFERRED EMBODIMENTS

Figure 4:
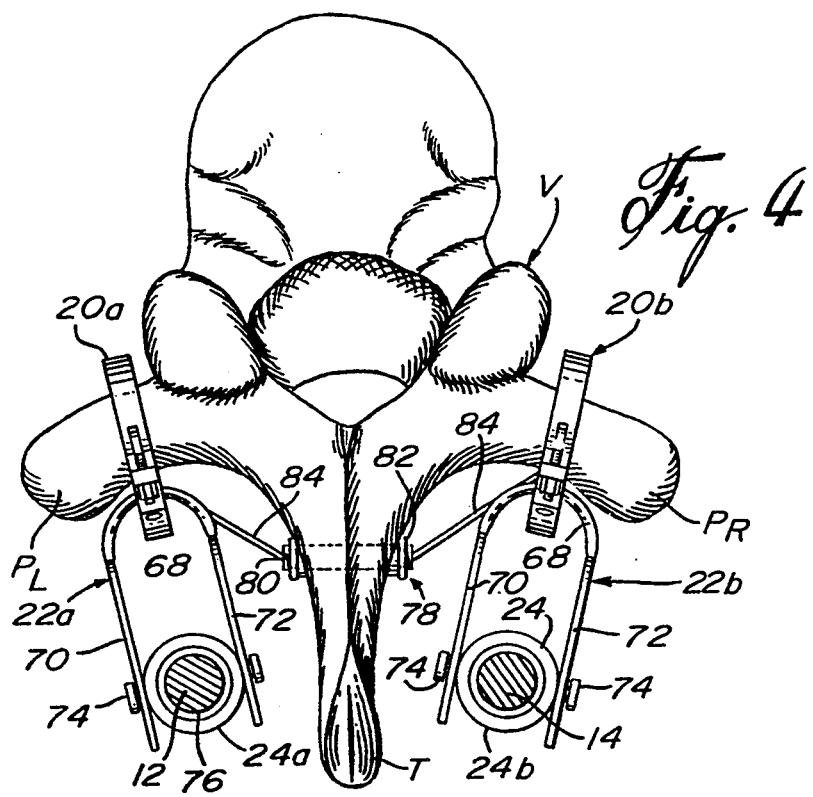
FIG. 4 is a top plan view of the embodiment shown in FIG. 3.

An internal brace system 10 is shown in FIGS. 1 and 2 in its assembled condition. The internal brace system 10 would be sold as a kit for implanting within the human body in a surgical procedure for the purpose of correcting a spinal column disorder involving a lateral curve with some torsion or rotation. It has been found that in patients suffering from scoliosis, that the vertebrae in the curved portion may be rotated horizontally due to torsional forces acting thereon. The internal brace system 10 would, as will be seen, retain the individual vertebra in a reoriented position approximating their position in a normal spinal column.

The kit making up the internal brace system 10 would include a pair of rods 12 and 14. Each of the rods 12 and 14 may be curved to approximate a desirable longitudinal curve of the portion of the spinal column in which the correcting system is to be implanted. The rods 12 and 14 would, when assembled, include bars 16 and 18 which lock the rods 12 and 14 in a unitary structure and act as a first means for rigidly connecting the rods 12, 14 in a spaced parallel arrangement. The rods 12 and 14 are preferably made of titanium.

The spinal column S to which the internal brace system is to be applied includes a number of vertebrae $V_a \ldots V_n$, each including, for the purposes of this description transverse processes $P_L$ and $P_R$ and a spinous process T. The vertebrae $V_a \ldots V_n$ would, in a patient suffering from scoliosis be curved laterally out of a longitudinal plane of the spine S and it would be necessary to rotate and realign each vertebra in longitudinal alignment and to be harnessed to the internal brace system 10.

In the present embodiment, the internal brace system 10 includes, a plurality of cuffs or anchor means 20 which can be mounted to individual transverse processes P and tie means in the form of U-shape tie members 22 connecting the cuffs 20 in an articulated manner to individual sleeves 24 slidably mounted on the rods 12 and 14.

Figure 3:
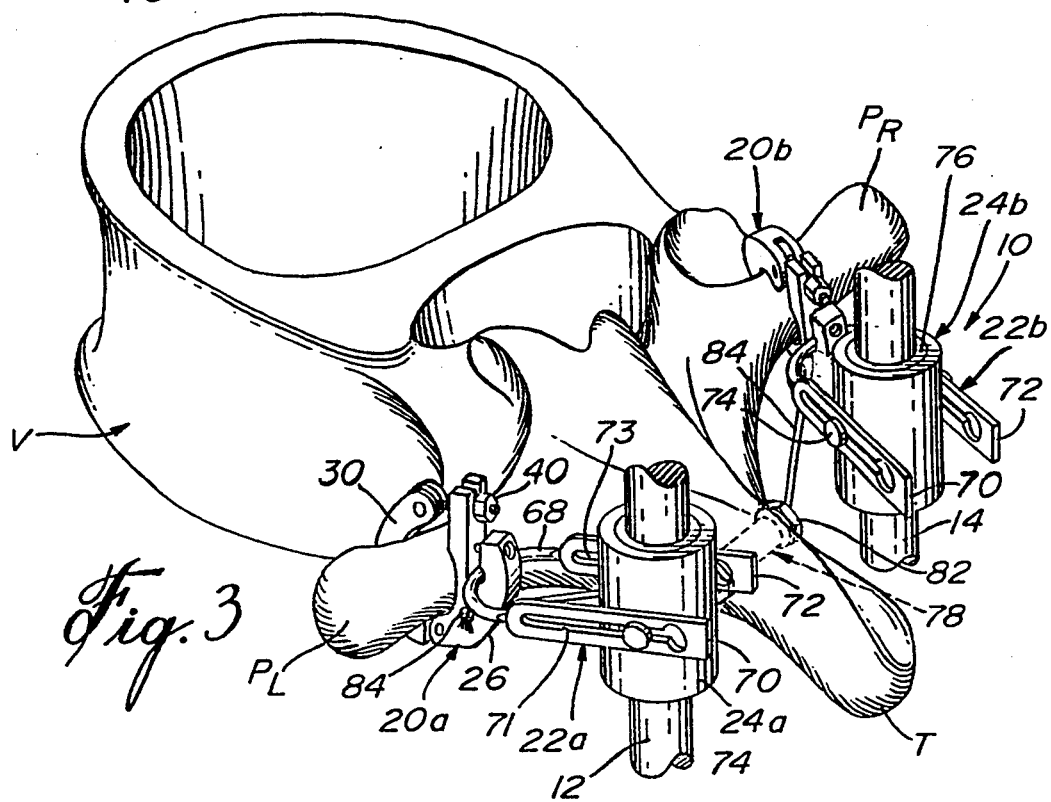
FIG. 3 is a fragmentary perspective view showing a single vertebra and details of the internal brace system in relation to the vertebra.

Referring now to FIGS. 3 and 4, the vertebra harness will be described in more detail. As shown in FIGS. 3 and 4, there is a cuff 20a which is clasped to the transverse process $P_L$ and an identical cuff 20b clasps to the transverse process $P_R$. The U-shaped tie 22a connects the cuff 20a to the sleeve 24a on rod 12. Likewise the U-shape tie member 22b connects the cuff 20b to the sleeve 24b on rod 14.

The cuff 20 is shown, in FIGS. 5 and 6, in detail and includes a base member 26 and a pair of arms 28 and 30 with hinges 32 and 34 therebetween. A locking pin 36 is hinged to the arm 30 by means of hinge 38. The pin 36 is threaded and adapted to receive a nut 40. The nut 40 locks the pin to the base 26 as shown in FIGS. 5 and 6. Accordingly the cuff 20 will be able to fit any irregularity or size of transverse process because of the particular adjustable structure shown. The base 26 also has a jaw 42 to receive the bight portion 68 of the U-shaped tie 22. A locking bolt 44 will close the jaw 42 once the bight 68 has been mounted in the jaw 42.

The tie member 22 is best shown in FIGS. 3 and 4 and includes a bight 68 with a pair of parallel arms 70 and 72. These arms 70 and 72 include slots 71 and 73 which engage the cap pins 74 on sleeve 24. The slots 71 and 73 are provided with enlarged openings at the ends thereof in order for the arms 70 and 72 to be engaged on the cap pins 74. Accordingly the construction of the tie member 22 allows articulation and a degree of lateral movement to the vertebra V. However, since both transverse processes $P_L$ and $P_R$ are likewise anchored to the respective rods 12 and 14 the amount of horizontal rotation of the vertebra V will be very limited.

It is also believed that the structure will retain the vertebra in its assumed position approximating a normal position of the vertebra in a correct spinal column.

In order to prevent the cuffs 20a and 20b from slipping off the ends of the transverse processes $P_L$ and $P_R$ an anchor tube 78 will be provided on the spinous process T. In one embodiment a bore is drilled through the spinous process T and the anchor tube 78 is fitted therein. Locking nuts 80 and 82 are provided at each end of the tube 78 and a flexible cord of synthetic material such as nylon is attached to each cuff 20a and 20b as shown in FIGS. 3, 5, and 6. Thus the cord 84 will prevent the cuffs 20a and 20b from slipping off the ends of the transverse processes.

The internal brace system 10 is selected to be long enough to be coextensive with the portion of the spinal column S which is to be corrected. The ends of the rods 12 and 14 are provided with heads 67 of square cross-section as shown, for instance, in FIG. 7. The square heads 67 of the rods 12 and 14 will accommodate a modified version of the cuffs as shown in FIG. 7. The cuff 46 in FIG. 7 includes the articulated arms 50 and 52 as well as a locking pin 58 and nut 60. However, the base 48 will also include a tube 64 (rigid tie means) having a bore or opening 66 which has a square cross-section similar to the square cross-section of the head 67 of the rod 12.

The base 48 will have a length which is selected depending on the distance of the internal brace system 10 from a correct vertebra as shown in FIG. 2. Likewise, at the other end of the rod 12, a similar cuff 46a will be locked to a transverse process $P_L$ of a correct vertebra. Thus, the internal brace assembly system 10 will be locked at each end to a correct vertebra, in this case the vertebra $V_b$ and $V_n$ while the vertebrae to be realigned are harnessed by means of the cuffs 20a and 20b and tie members 22 connected on the sliding sleeve 24a and 24b.

The provision of the sliding sleeves 24 and flexible ties 22 will allow limited movement of each vertebra and will allow the loads to be carried by the realigned spinal column S so as to simulate a more normal spinal column. The sleeve may have a polyethylene liner 76 to reduce friction.

The bars 16 and 18 are provided with bores of square cross-section at each end thereof. These bores are dimensioned to the square heads 67 of the rods 12 and 14, and with suitable set screws 13 the bars 16 and 18 can be locked to the ends of rods 12 and 14.

When the internal brace system 10 is implanted, it is necessary to sever certain ligaments particularly between the spinous processes. It has been contemplated to attach biodegradable polymer ligaments between the spinous processes and probably between respective transverse processes. The polymer material, in one example, could include from 0% to 30% hydroxyvalerate and from 100% to 70% polyhydroxybutyrate. Ligaments of this material would slowly degrade while natural ligaments are regenerated. The material and its uses are described in G.B. Patent 1034 123 in the name of W. R. Grace & Co.

I claim:

1. An internal brace system comprising:
    a pair of implantable rods adapted to be on either side of a spinal column coextensive with a portion of the spinal column to be treated; first connecting means for rigidly connecting said rods together in a spaced-apart parallel arrangement to provide a unitary internal brace structure; pairs of anchor means for engaging a corresponding one of a plurality of selected vertebrae, each of said anchor means of each of said pairs of anchor means being adapted to be disposed on respective transverse processes of the corresponding one of said plurality of selected vertebrae in the portion of the spinal column to be treated; second connecting means for connecting to a respective rod of the internal brace structure on either side of the spinal column; first tie means for extending from each of said anchor means to respective ones of said second connecting means, said first tie means being articulated to allow relative movement of said corresponding one of said anchor means while retaining said anchor means in a predetermined location relative to the internal brace structure and through the selected vertebrae against torsional forces applied through the spinal column.

2. An internal brace system as defined in claim 1, wherein each of said anchor means are in the form of a cuff adapted to be mounted on a respective transverse process and the first tie means includes rigid link members articulately connected to each cuff.

3. An internal brace system as defined in claim 2, wherein each cuff includes a base portion and at least a pair of articulated arms extending from the base portion and adapted to be locked forming a loop with adjustable locking means to vary the size and shape of the loop to accommodate the respective transverse process of said corresponding one of the plurality of vertebrae.

4. An internal brace system as defined in claim 2, further comprising second anchor means adapted to be attached to a spinous process of at least one of the plurality of selected vertebrae and second tie means extending between the cuffs associated with the at least one of the plurality of selected vertebrae and the second anchor means for preventing said cuffs associated with the at least one of the plurality of selected vertebrae from slipping off the respective transverse processes.

5. An internal brace system as defined in claim 4, wherein the second tie means is in the form of a flexible, strong cord, the second anchor means for the spinous process includes a tube which is adapted to pass through the spinous process and means for locking the tube to the spinous process and the flexible cord extends through the tube such that each end of the flexible cord is connectable to one of said cuffs associated with at least one of the plurality of selected vertebrae.

6. An internal brace system as defined in claim 2, wherein the second connecting means on the rods are in the form of sleeves adapted to slide on the rods with each separate sleeve corresponding to a respective first tie means extending from each anchor means on the respective transverse process of the corresponding one of said plurality of said selected vertebrae.

7. An internal brace system as defined in claim 6, wherein each of said respective first tie means includes a rigid U-shaped bracket having a bight portion adapted to be engaged in an articulate manner with said cuff, the U-shaped bracket including a pair of parallel arms extending from the bight and each of said arms including an elongated slot adapted to be engaged on a cap pin on respective portions of each of said separate sleeves such that the brace system can slide relative to said separate sleeves.

8. An internal brace system as defined in claim 2, wherein the first connecting means for rigidly connecting the rods is in the form of detachable bars extending between the rods at each end of the rods thereof and rigid second tie means on each end cuff are connected directly to the ends of the rods for providing a rigid connection between each of the end cuffs associated with each of said plurality of selected vertebrae corresponding to the ends of the rods and the rods.

9. An internal brace system as defined in claim 8, further comprising locking set screws and wherein the ends of the rods have a square cross-section, said first bar means for rigidly connecting said rods together includes said detachable bars each having bores with a cross-section approximately the same as the square cross-section of the rods and said locking set screws lock the rods in the bores of the detachable bars providing the unitary structure.

10. An internal brace system as defined in claim 1, wherein the rods are made of titanium.

11. An internal brace system comprising: a pair of implantable rods adapted to be mounted on either side of a spinal column coextensive with a portion of the spinal column to be treated; first connecting means for rigidly connecting said rods together in a spaced-apart parallel arrangement to provide a unitary internal brace structure; pairs of anchor means for engaging a corresponding one of a plurality of selected vertebrae, each of said anchor means of each of said pairs of anchor means adapted to be disposed on respective transverse processes of the corresponding one of said plurality of selected vertebrae in the portion of the spinal column to be treated; second connecting means for connecting to a respective rod of the internal brace structure on either side of the spinal column; first tie means for extending from each of said anchor means to respective ones of said second connecting means, said first tie means articulately connected to said corresponding one of said plurality of said anchor means while retaining said corresponding one of said anchor means in a predetermined location relative to the internal brace structure and against torsional forces applied through the spinal column.

* * * * *